(12) United States Patent
Zhang et al.

(10) Patent No.: US 9,937,477 B2
(45) Date of Patent: Apr. 10, 2018

(54) ENCAPSULATION

(71) Applicant: Encapsys, LLC, Appleton, WI (US)

(72) Inventors: Hanwei Zhang, Appleton, WI (US);
Todd Arlin Schwantes, Lena, WI (US);
Katie Ann Hobart, Neenah, WI (US);
Diane Jean Williamson, Kaukauna, WI (US)

( * ) Notice: Subject to any disclaimer, the term of this patent is extended or adjusted under 35 U.S.C. 154(b) by 0 days.

(21) Appl. No.: 15/334,540

(22) Filed: Oct. 26, 2016

(65) Prior Publication Data

US 2017/0113200 A1   Apr. 27, 2017

Related U.S. Application Data

(60) Provisional application No. 62/246,805, filed on Oct. 27, 2015.

(51) Int. Cl.
*A01N 25/28* (2006.01)
*A61K 9/50* (2006.01)
(Continued)

(52) U.S. Cl.
CPC .............. *B01J 13/18* (2013.01); *A01N 25/28* (2013.01); *A61K 8/11* (2013.01); *A61K 8/8152* (2013.01);
(Continued)

(58) Field of Classification Search
CPC ......... B01J 13/18; B01J 13/14; F28D 20/023; C09B 67/0097; A61K 9/50; A61K 8/11;
(Continued)

(56) References Cited

U.S. PATENT DOCUMENTS 4,847,152 A   7/1989  Jabs et al.
7,968,197 B2  6/2011  Barancyk et al.
(Continued)

FOREIGN PATENT DOCUMENTS

CA   2 302 235   3/1999
EP   1 693 104   8/2006
(Continued)

OTHER PUBLICATIONS

Polenz et al., "Polyurea Microcapsules in Microfluidics: Surfactant Control of Soft Membranes," Langmuir 2015, 31, 1127-1134.*
(Continued)

*Primary Examiner* — Aradhana Sasan
(74) *Attorney, Agent, or Firm* — Benjamin Mieliulis

(57) ABSTRACT

An improved process of making a benefit agent delivery particle and an improved microcapsule made by such process are disclosed. The process comprises the steps of providing a first composition of water phase 1, water phase 2 and water phase 3. Water phase 1 comprises water and an initiator; water phase 2 comprises water, a water-soluble or dispersible amine(meth)acrylate or hydroxyl(meth)acrylate and a multifunctional (meth)acrylate. Water phase 3 comprises water, and carboxyalkyl(meth)acrylate and a base or quarternary ammonium acrylate. The first two water phases are combined to prereact the hydroxy- or amine(meth) acrylate and the multifunctional (meth)acrylate to form a multifunctional hydroxyl-amine(meth)acrylate pre-polymer. The pre-polymer is combined with water phase 3; then an emulsion is formed by emulsifying under high shear agitation a second composition into said first composition; said second composition comprising an oil phase comprising an isocyanate and a benefit agent core material thereby forming a wall surrounding the benefit agent core material.

31 Claims, 3 Drawing Sheets

(51) Int. Cl.
| | |
|---|---|
| *A61K 8/11* | (2006.01) |
| *A61K 8/81* | (2006.01) |
| *A61K 8/88* | (2006.01) |
| *A61Q 15/00* | (2006.01) |
| *A61Q 17/04* | (2006.01) |
| *A61Q 13/00* | (2006.01) |
| *B01J 13/18* | (2006.01) |
| *B01J 13/14* | (2006.01) |
| *C09B 67/02* | (2006.01) |
| *C10M 171/06* | (2006.01) |
| *C11D 3/50* | (2006.01) |
| *F28D 20/02* | (2006.01) |

(52) U.S. Cl.
CPC ............... *A61K 8/88* (2013.01); *A61K 9/50* (2013.01); *A61K 9/5026* (2013.01); *A61K 9/5031* (2013.01); *A61K 9/5089* (2013.01); *A61Q 13/00* (2013.01); *A61Q 15/00* (2013.01); *A61Q 17/04* (2013.01); *B01J 13/14* (2013.01); *C09B 67/0097* (2013.01); *C10M 171/06* (2013.01); *C11D 3/505* (2013.01); *F28D 20/023* (2013.01); *C10N 2220/08* (2013.01); *C10N 2250/16* (2013.01)

(58) Field of Classification Search
CPC .. A61K 9/5026; A61K 9/5031; A61K 9/5089; A61K 8/8152; C11D 3/505; A61Q 15/00; A61Q 17/04; A61Q 13/00; C10M 171/06; A01N 25/28; C10N 2220/08; C10N 2250/16

See application file for complete search history.

(56) References Cited

U.S. PATENT DOCUMENTS

| | | | |
|---|---|---|---|
| 7,968,198 | B2 | 6/2011 | Barancyk et al. |
| 8,715,544 | B2 | 5/2014 | Schwantes |
| 8,927,026 | B2 | 1/2015 | Dihora et al. |
| 2002/0079599 | A1 | 6/2002 | Kleban et al. |
| 2008/0125552 | A1 | 5/2008 | Schocker et al. |
| 2009/0274905 | A1 | 11/2009 | Schwantes |
| 2011/0057340 | A1 | 3/2011 | Perichaud et al. |
| 2011/0269657 | A1 | 11/2011 | Dihora et al. |
| 2013/0089590 | A1 | 4/2013 | Hotz et al. |

FOREIGN PATENT DOCUMENTS

| | | |
|---|---|---|
| WO | WO 2012/007438 | 1/2012 |
| WO | WO 2012/075293 | 6/2012 |

OTHER PUBLICATIONS

International Search Report for PCT/US2016/058773.

* cited by examiner

ENCAPSULATION

FIELD OF THE INVENTION

This invention relates to capsule manufacturing processes and microcapsules produced by such processes.

DESCRIPTION OF THE RELATED ART

Various processes for microencapsulation, and exemplary methods and materials are set forth in Schwantes (U.S. Pat. No. 6,592,990), Nagai et al. (U.S. Pat. No. 4,708,924), Baker et al. (U.S. Pat. No. 4,166,152), Woiciak (U.S. Pat. No. 4,093,556), Matsukawa et al. (U.S. Pat. No. 3,965,033), Matsukawa (U.S. Pat. No. 3,660,304), Ozono (U.S. Pat. No. 4,588,639), Irgarashi et al. (U.S. Pat. No. 4,610,927), Brown et al. (U.S. Pat. No. 4,552,811), Scher (U.S. Pat. No. 4,285,720), Shioi et al. (U.S. Pat. No. 4,601,863), Kiritani et al. (U.S. Pat. No. 3,886,085), Jahns et al. (U.S. Pat. Nos. 5,596,051 and 5,292,835), Matson (U.S. Pat. No. 3,516,941), Chao (U.S. Pat. No. 6,375,872), Foris et al. (U.S. Pat. Nos. 4,001,140; 4,087,376; 4,089,802 and 4,100,103), Greene et al. (U.S. Pat. Nos. 2,800,458; 2,800,457 and 2,730,456), Clark (U.S. Pat. No. 6,531,156), Saeki et al. (U.S. Pat. Nos. 4,251,386 and 4,356,109), Hoshi et al. (U.S. Pat. No. 4,221,710), Hayford (U.S. Pat. No. 4,444,699), Hasler et al. (U.S. Pat. No. 5,105,823), Stevens (U.S. Pat. No. 4,197,346), Riecke (U.S. Pat. No. 4,622,267), Greiner et al. (U.S. Pat. No. 4,547,429), and Tice et al. (U.S. Pat. No. 5,407,609), among others and as taught by Herbig in the chapter entitled "Microencapsulation" in Kirk-Othmer Encyclopedia of Chemical Technology, V. 16, pages 438-463.

Other useful methods for microcapsule manufacture are: Foris et al., U.S. Pat. Nos. 4,001,140 and 4,089,802 describing a reaction between urea and formaldehyde; Foris et al., U.S. Pat. No. 4,100,103 describing reaction between melamine and formaldehyde; and British Pat. No. 2,062,570 describing a process for producing microcapsules having walls produced by polymerization of melamine and formaldehyde in the presence of a styrenesulfonic acid. Forming microcapsules from urea-formaldehyde resin and/or melamine formaldehyde resin is disclosed in U.S. Pat. Nos. Foris et al., U.S. Pat. No. 4,001,140; Foris et al., U.S. Pat. No. 4,089,802; Foris et al., U.S. Pat. No. 4,100,103; Foris et al., U.S. Pat. No. 4,105,823; and Hayford, U.S. Pat. No. 4,444,699. Alkyl acrylate-acrylic acid copolymer capsules are taught in Brown et al., U.S. Pat. No. 4,552,811. Each patent described throughout this application is incorporated herein by reference to the extent each provides guidance regarding microencapsulation processes and materials.

Interfacial polymerization is a process wherein a microcapsule wall or polyamide, an epoxy resin, a polyurethane, a polyurea or the like is formed at an interface between two phases. Riecke, U.S. Pat. No. 4,622,267 discloses an interfacial polymerization technique for preparation of microcapsules. The core material is initially dissolved in a solvent and an aliphatic diisocyanate soluble in the solvent mixture is added. Subsequently, a nonsolvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurethane shells. A similar technique, used to encapsulate salts which are sparingly soluble in water in polyurethane shells, is disclosed in Greiner et al., U.S. Pat. No. 4,547,429. Matson, U.S. Pat. No. 3,516,941 teaches polymerization reactions in which the material to be encapsulated, or core material, is dissolved in an organic, hydrophobic oil phase which is dispersed in an aqueous phase. The aqueous phase has dissolved materials forming aminoplast (amine and aldehyde) resin which upon polymerization form the wall of the microcapsule. A dispersion of fine oil droplets is prepared using high shear agitation. Addition of an acid catalyst initiates the polycondensation forming the aminoplast resin within the aqueous phase, resulting in the formation of an aminoplast polymer which is insoluble in both phases. As the polymerization advances, the aminoplast polymer separates from the aqueous phase and deposits on the surface of the dispersed droplets of the oil phase to form a capsule wall at the interface of the two phases, thus encapsulating the core material. Urea-formaldehyde (UF), urea-resorcinol-formaldehyde (URF), urea-melamine-formaldehyde (UMF), and melamine-formaldehyde (MF), capsule formations proceed in a like manner. In interfacial polymerization, the materials to form the capsule wall are in separate phases, one in an aqueous phase and the other in an oil phase. Polymerization occurs at the phase boundary. Thus, a polymeric capsule shell wall forms at the interface of the two phases thereby encapsulating the core material. Wall formation of polyester, polyamide, and polyurea capsules also typically proceed via interfacial polymerization.

Jahns, U.S. Pat. No. 5,292,835 teaches polymerizing esters of acrylic acid or methacrylic acid with polyfunctional monomers. Specifically illustrated are reactions of polyvinylpyrrolidone with acrylates such as butanediol diacrylate or methylmethacrylate together with a free radical initiator.

Common microencapsulation processes can be viewed as a series of steps. First, the core material which is to be encapsulated is typically emulsified or dispersed in a suitable dispersion medium. This medium is typically aqueous but involves the formation of a polymer rich phase. Most frequently, this medium is a solution of the intended capsule wall material. The solvent characteristics of the medium are changed such as to cause phase separation of the wall material. The wall material is thereby contained in a liquid phase which is also dispersed in the same medium as the intended capsule core material. The liquid wall material phase deposits itself as a continuous coating about the dispersed droplets of the internal phase or capsule core material. The wall material is then solidified. This process is commonly known as coacervation.

The capsules according to the invention are useful with a wide variety of capsule contents ("core materials") including, by way of illustration and without limitation, internal phase oils, solvent oils, phase change materials, lubricants, dyes, perfumes, fragrances, cleaning oils, polishing oils, flavorants, nutrients, sweeteners, chromogens, pharmaceuticals, fertilizers, herbicides, biological actives, scents, and the like. The microcapsule core materials can include materials which alter rheology or flow characteristics, or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, 16B, leuco dyes, all by way of illustration and not limitation. The core material typically should be dispersible or sufficiently soluble in the capsule internal phase material namely in the internal phase oil or soluble or dispersible in the monomers or oligomers solubilized or dispersed in the internal phase oil. The core materials are preferably liquid but can be solid depending on the materials selected, and with temperatures appropriately adjusted to effect dispersion.

Jabs et al., U.S. Pat. No. 4,947,152 teaches microcapsules with polyurea walls. The wall is the reaction product of an aromatic isocyanate with an isocyanate reactive group. The isocyanate reactive group can include di- and polyamines such as N-hydroxyethylethylenediamine, ethylene-1,2-diamine.

Hotz et al., U.S. Pat. Pub. 2013/0089590 teaches a fragrance microcapsule with a polyurea wall. The shell in the reaction product of at least two difunctional isocyanates and a difunctional amine.

EP 1693104 Maruyyama discloses microcapsules having a polyurethane or polyurea wall obtained from polycondensation of a polyfunctional isocyanate with a polyfunctional amine.

Schwantes, U.S. Pat. Pub. 2009/0274905 teaches cationic microcapsule particles where the wall in the reaction product of an amine acrylate with a multifunctional methacrylate in the presence of an acid and initiator; or alternatively an acid acrylate and multifunctional (meth)acrylate in the presence of a base and initiator.

A need has existed in the art for polyurea or urethane type microcapsules which are robust, which retain capsule contents over time, or until fractured or otherwise made permeable.

The above references do not teach that an improved microcapsule can be achieved comprising a core, the shell being a product of a reaction mixture of a first component comprising an isocyanate; and a second component comprising a water dispersible oligomerized multifunctional amine (meth)acrylate together with a carboxyalkyl(meth)acrylate to yield a robust microcapsule which is resistant to breakage and resistant to solvents. The microcapsules are useful in a variety of challenging environments, such as use with fabric enhancers, laundry, phase change and other industrial and commercial applications.

Definition

As used herein, reference to the term "(meth)acrylate" or "(meth)acrylic" is to be understood as referring to both the acrylate and the methacrylate versions of the specified monomer, oligomer and/or prepolymer, (for example "allyl (meth)acrylate" indicates that both allyl methacrylate and allyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible). Each alkyl moiety herein, unless otherwise indicated, can be from $C_1$ to $C_8$, or even from $C_1$ to $C_{24}$. Poly(meth)acrylate materials are intended to encompass a broad spectrum of polymeric materials including, for example, polyester poly(meth)acrylates, urethane and polyurethane poly(meth)acrylates (especially those prepared by the reaction of an hydroxyalkyl (meth)acrylate with a polyisocyanate or a urethane polyisocyanate), methylcyanoacrylate, ethylcyanoacrylate, diethyleneglycol di(meth)acrylate, trimethylolpropane tri(meth) acrylate, ethylene glycol di(meth)acrylate, allyl (meth) acrylate, glycidyl (meth)acrylate, (meth)acrylate functional silicones, di-, tri- and tetraethylene glycol di(meth)acrylate, dipropylene glycol di(meth)acrylate, polyethylene glycol di(meth)acrylate, di(pentamethylene glycol) di(meth)acrylate, ethylene di(meth)acrylate, neopentyl glycol di(meth) acrylate, trimethylolpropane tri(meth)acrylate, ethoxylated bisphenol A di(meth)acrylates, bisphenol A di(meth)acrylates, diglycerol di(meth)acrylate, tetraethylene glycol dichloroacrylate, 1,3-butanediol di(meth)acrylate, neopentyl di(meth)acrylate, trimethylolpropane tri(meth)acrylate, polyethylene glycol di(meth)acrylate and dipropylene glycol di(meth)acrylate and various multifunctional (meth)acrylates and multifunctional amine (meth)acrylates. Monofunctional acrylates, i.e., those containing only one acrylate group, may also be advantageously used. Typical monoacrylates include 2-ethylhexyl (meth)acrylate, 2-hydroxyethyl (meth)acrylate, cyanoethyl (meth)acrylate, 2-hydroxypropyl (meth)acrylate, p-dimethylaminoethyl (meth)acrylate, lauryl (meth)acrylate, cyclohexyl (meth)acrylate, tetrahydrofurfuryl (meth)acrylate, chlorobenzyl (meth)acrylate, aminoalkyl (meth)acrylate, various alkyl(meth)acrylates and glycidyl (meth)acrylate. Of course mixtures of (meth)acrylates or their derivatives as well as combinations of one or more (meth)acrylate monomers, oligomers and/or prepolymers or their derivatives with other copolymerizable monomers, including acrylonitriles and methacrylonitriles may be used as well.

SUMMARY OF THE INVENTION

Figure 1:
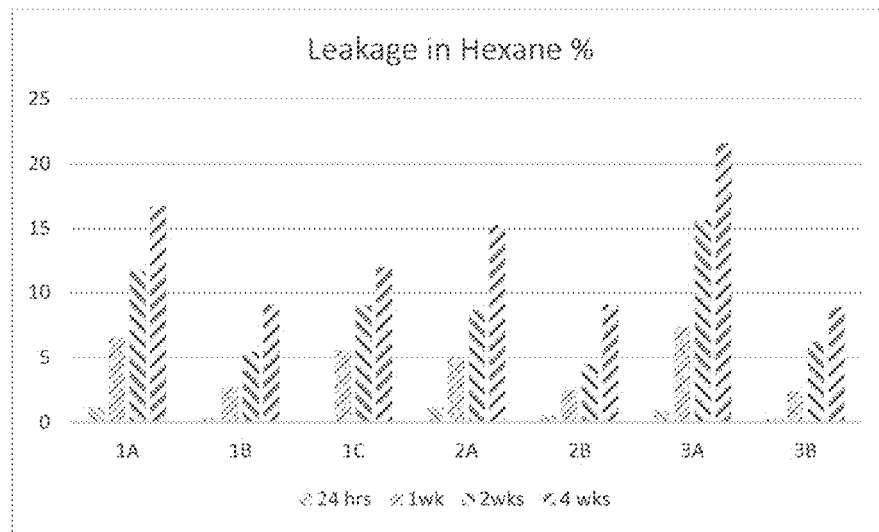
FIG. 1 charts leakage in hexane of microcapsules of Example 8
Figure 2:
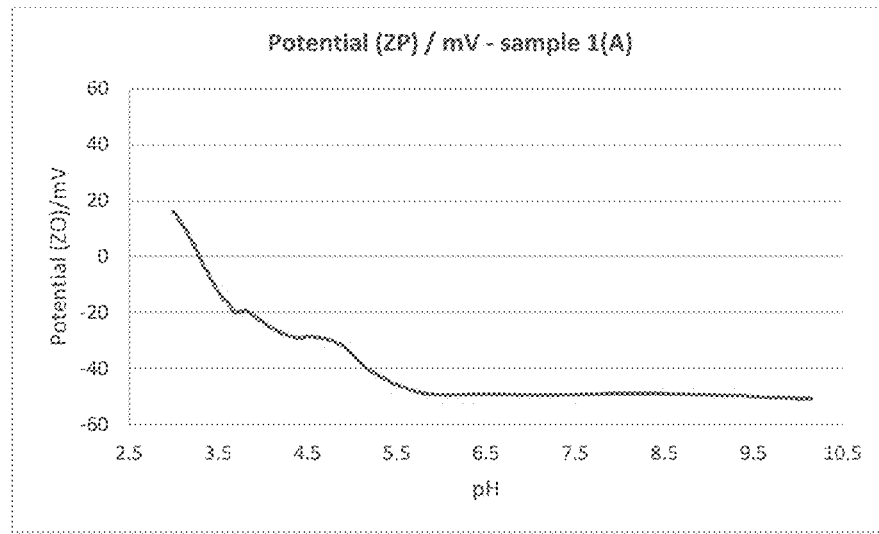
FIGS. 2, 3, 4, 5 and 6 chart zeta potential of samples described in Example 8.
Figure 3:
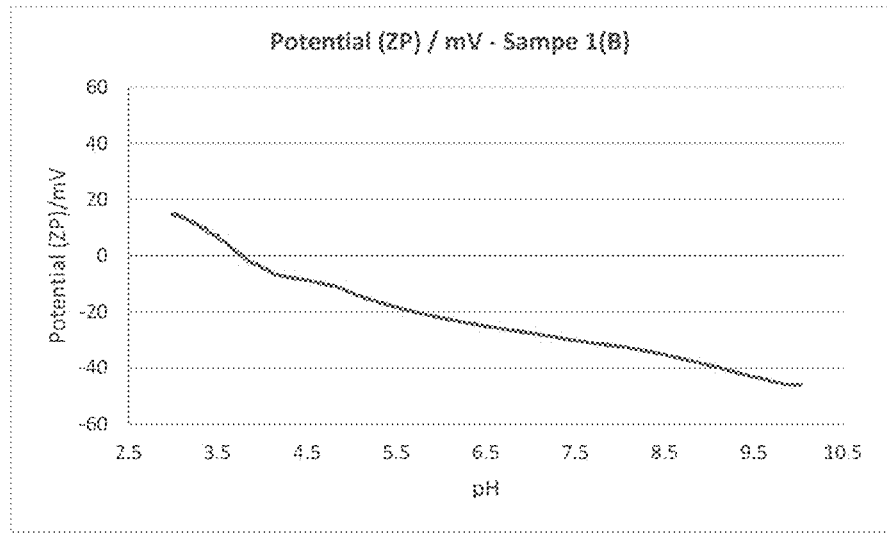
Figure 4:
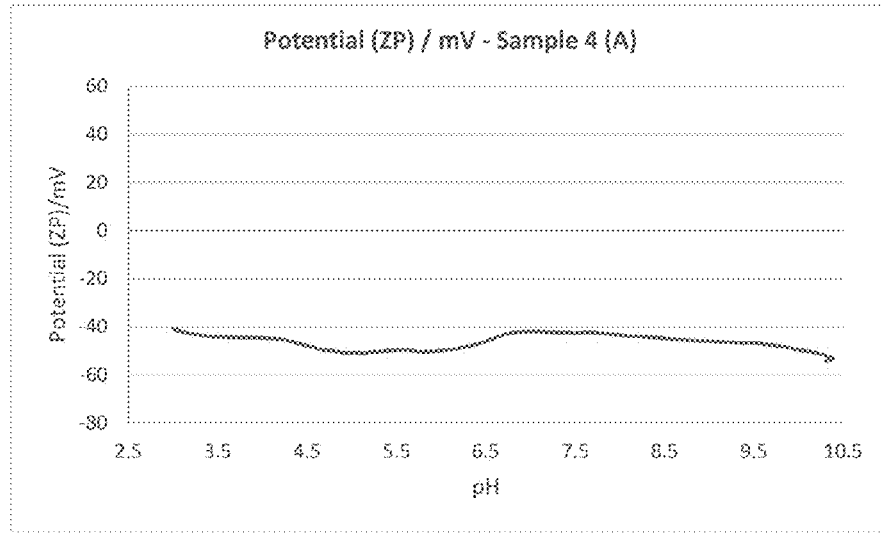
Figure 5:
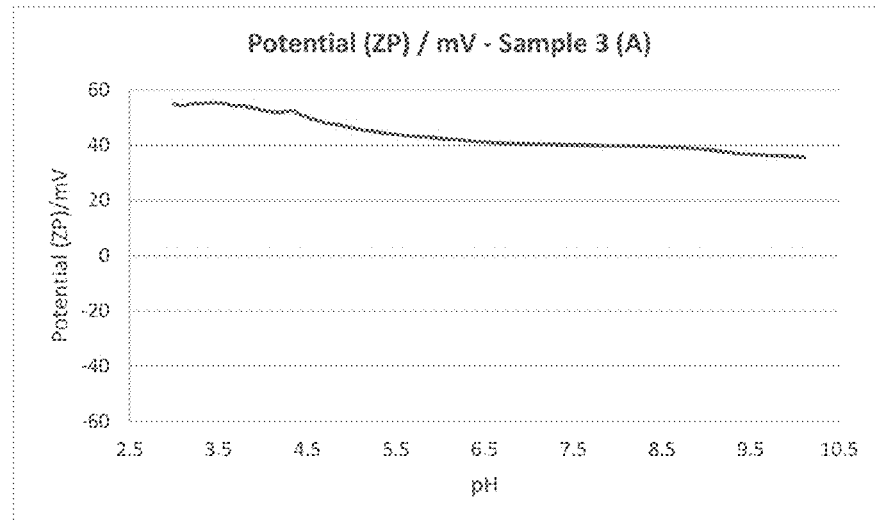
Figure 6:
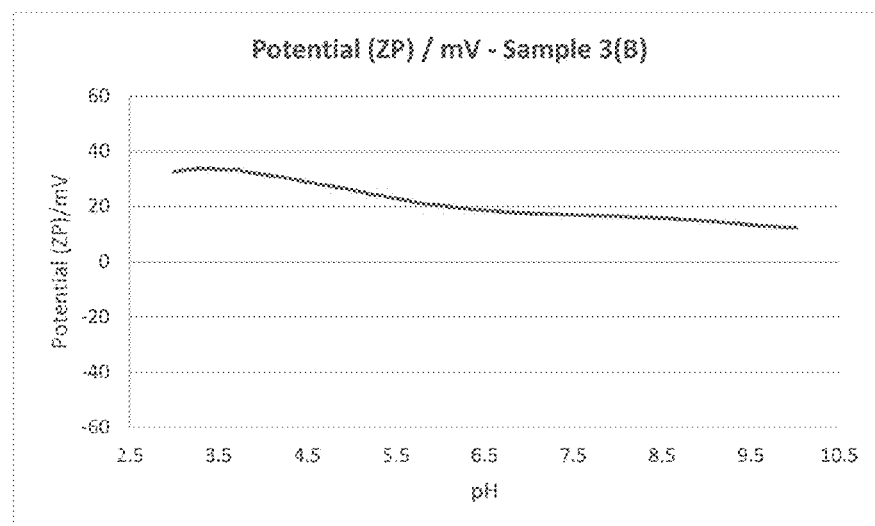

The present invention comprises a microcapsule comprising a core, and a shell surrounding the core material, the shell comprising a reaction product of a first component comprising an isocyanate; and a second component comprising one or more poly(meth)acrylates, more particularly, a multifunctional amine (meth)acrylate, wherein the multifunctional amine (meth)acrylate is selected to be polar and reactive with the isocyanate. Optionally but preferably, a carboxyalkyl(meth)acrylate is blended with the multifunctional amine(meth)acrylate. In the invention, the capsule wall material has as a major component a polyurethane or polyurea, and as a minor component, an acrylate prepolymer or polymer In one aspect the invention comprises a microcapsule comprising an oil soluble or dispersible benefit agent core material and a shell surrounding the benefit agent core material, the shell comprising a polyurea formed from a first component of an isocyanate and a second component of an amine, the amine comprising the reaction product of a poly(meth)acrylate, more particularly, an alkylaminoalkyl (meth)acrylate and a multifunctional (meth)acrylate, reacted with a carboxyalkyl(meth)acrylate.

In another aspect the invention comprises a microcapsule wherein the shell comprises a reaction product of an isocyanate; and a multifunctional amine (meth)acrylate.

In a further embodiment, the microcapsule second component multifunctional amine (meth)acrylate is an oligomer, or alternatively, the isocyanate is an oligomer.

The mole ratio of isocyanate groups of the first component as compared to the amine or hydroxyl groups of the second component is in the range from 0.5:1 to about 20:1.

The core comprises a benefit agent core material.

In a yet further embodiment, the invention comprises a process of making a benefit agent delivery particle, the process comprising heating in one or more steps, an emulsion, said emulsion produced by emulsifying the combination of a first composition formed by combining a water phase 1, a water phase 2, and a water phase 3;

said water phase 1 comprising water and an initiator;

said water phase 2 comprising water, hydroxyalkyl(meth) acrylate and a multifunctional (meth)acrylate;

said water phase 3 comprising water and carboxyalkyl (meth)acrylate, and a base;

and a second composition, said second composition comprising an oil phase comprising an isocyanate and a core material.

In a further embodiment, the invention comprises a microcapsule comprising an oil soluble or dispersible benefit agent core material and a shell surrounding the benefit agent core material. The shell comprises a polyurethane formed from a first component of an isocyanate and a second component of a polyol. The polyol comprises the reaction product of a hydroxy(meth)acrylate and a multifunctional (meth)acrylate, together with a carboxyalkyl(meth)acrylate or quarternary ammonium acrylate.

In one embodiment the polyol is a hydroxy(meth)acrylate, more particularly a hydroxyalkyl(meth)acrylate such as hydroxyethyl(meth)acrylate.

Alternatively, the shell comprises a reaction product of an isocyanate; and a multifunctional hydroxyl(meth)acrylate.

The isocyanate in one embodiment can be selected from isophorone diisocyanate, 4,4'-methylene diphenyl diisocyanate, 2,2'-methylene diphenyl diisocyanate, and 2,4'-methylene diphenyl diisocyanate.

Alternatively, the polyol can be hydroxyalkyl(meth)acrylate wherein each alkyl moiety independently is from $C_1$ to $C_8$ or even $C_1$ to $C_{24}$.

In a further embodiment the hydroxy(meth)acrylate is selected from hydroxyalkyl(meth)acrylate, alkylene glycol (meth)acrylate and glycerol 1,3-diglycerate diacrylate.

The microcapsules of the invention display high strength, and low leakage in environments such as in contact with solvents, detergents, shampoos, fabric softeners, and surface cleaners. As a result, the microcapsules of the invention are suitable for use in such products by being able to survive in such environments.

In addition, the microcapsules of the invention, such as when the core is selected to be a phase change material (latent heat material), can be advantageously employed in products such as microcapsules in mattresses, pillows, bedding, textiles, sporting equipment, medical devices, building products, construction products, heat and ventilating applications (HVAC), renewable energy applications, solar panels, clothing, athletic surfaces, automotive, aviation, shoes, beauty care, laundry and solar energy products.

The present invention discloses a microcapsule having a wall with a surface charge, the microcapsule made by a process comprising dispersing in one or more water phases an initiator, and a cross-linking functional monomer having one or more —OH, —NH$_2$, or —NH— groups, and a charge functional monomer having anionic or cationic groups selected from carboxyl, sulfonic acid groups or quaternary ammonium groups, or other charged groups.

The monomers in the one or more water phases are prereacted and combined with a water dispersible multifunctional (meth)acrylate monomer.

An emulsion is formed by emulsifying into the water phase or phases, using high shear agitation, an oil phase comprising an isocyanate and a benefit agent core material.

Optionally, additional cross-linker such as compounds containing 2 or more primary or secondary amine groups may be added. The combined emulsion of prereacted monomers, water dispersible multifunctional (meth)acrylate monomer, and oil phase are further reacted by heating or actinic irradiation for a time, and temperature or irradiation sufficient to form a microcapsule wall surrounding the benefit agent core material.

Advantageously the cross-linking functional monomer having an —OH, —NH$_2$, or —NH— group can be an amine, such as an alkylaminoalkyl(meth)acrylate.

Alternatively, the cross-linking functional monomer having an —OH, —NH$_2$, or —NH⁻ group can be a hydroxyl group such as that existing in hydroxyl(meth)acrylate.

Optionally after microcapsule wall formation, the formed microcapsule can be isolated from the water phase or continuous phase, such as by decanting, dewatering, centrifuging, spray-drying, evaporation, freeze drying or other solvent removal or drying process.

DETAILED DESCRIPTION

The present invention discloses a composition and process of forming a population of microcapsules. The microcapsules comprise an oil soluble or dispersible benefit agent core material and a shell surrounding the benefit agent core material. The shell comprises the reaction product of an isocyanate and a multifunctional amine (meth)acrylate. The multifunctional amine (meth)acrylate can be selected to be polar and reactive with the isocyanate.

The process of the invention is based on formation of an oil-in-water emulsion to effect encapsulation. The invention comprises a microcapsule comprising an oil soluble or dispersible benefit agent core material and a shell surrounding the benefit agent core material, the shell comprising a polyurea formed from a first component of an isocyanate and a second component of a cross-linking functional polymer or oligomer having cross-linking functional groups such as —OH, —NH$_2$, or —NH⁻. When the second component is an amine, the amine comprises the reaction product of an alkylaminoalkyl(meth)acrylate and a multifunctional (meth) acrylate, together with a charge functional monomer such as carboxyalkyl(meth)acrylate or quarternary ammonium acrylate.

The cross-linking functional monomer such as, for example, hydroxyethylmethacrylate, 2-tert-(butylamino) ethyl methacrylate or 2-aminoethyl methacrylate is selected to be water soluble and have cross-linking functional groups.

The charge functional monomer such as 2-(methacryloyloxy ethyl) trimethyl ammonium chloride or a carboxyalkyl (meth)acrylate is also selected to be water soluble.

The multifunctional monomer is also selected to be water dispersible and selected from materials such as ethoxylated trimethylolpropane triacrylate, or polyethylene glycol diacrylate, or polyethylene glycol dimethacrylate.

To effect the block polymerization a pre-initiation step is employed in a preheating step with initiator and the reactive cross-linking functional monomer and multifunctional acrylate to form an acrylate pre-polymer. The pre-polymer is further reacted with the charge functional monomer to yield a block polymer.

Emulsification is carried out without the necessity of substantial addition of emulsifier such as polyvinyl alcohol. The emulsifier thereby is optional.

Optional additional cross-linker can be added after emulsification. Such compounds contain two or more primary or secondary amine groups and can be selected from various amine cross-linkers known in the art, including without limitation, cross-linkers such as ethylenediamine, diethylenetriamine, triethylenetetramine, tetraethylenepentamine, or pentaethylenehexamine. Other exemplary cross-linkers can include N-(methylisoamyl)ethylenediamine, N-(benzyl)ethylenediamine, N-(2-ethylhexyl)ethylenediamine, N-(isopropyl)ethylenediamine, N-(4-methylbenzyl)ethylenediamine, N-(3-methylbenzyl)ethylenediamine, N-(2-methylbenzyl)ethylenediamine, N-(4-methoxybenzyl)ethylenediamine, N-(3-methoxybenzyl)ethylenediamine, N-(2-methoxybenzyl)ethylenediamine, N-(2-methyl propyl)ethylenediamine, N-(2-methylbutyl)ethylenediamine, N-(methyl-propyl)ethylenediamine, N-(sec-butyl)ethylenediamine, N-(sec-phenylethyl)ethylenediamine, N-(tert-butyl)ethylenediamine, N,N'''-bis-(methylisoamyl)triethylenetetramine, N,N'''-bis-(benzyl)triethylenetetramine, N,N'''-bis-(2-ethylhexyl)triethylenetetramine, N,N'''-bis-(isopropyl)triethylenetetramine, N,N'''-bis(4-methylbenzyl)triethylenetetramine, N,N'''-bis-(3-methylbenzyl)triethylenetetramine, N,N'''-bis-(2-methylbenzyl)triethylenetetramine, N,N'''-bis-(4-methoxybenzyl)triethylenetetramine, N,N'''-bis-(3-methoxybenzyl)triethylenetetramine, N,N'''-bis(2-methoxybenzyl)triethylenetetramine, N,N'''-bis-(2-methylpropyl)triethylenetetramine, N,N'''-bis-(2-methylbutyl)triethylenetetramine, N,N'''-bis-(methyl-propyl)triethylenetetramine, N,N'''-bis-(sec-butyl)triethylenetetramine, N,N'''-bis-(sec-phenylethyl)triethylenetetramine, N,N'''-bis-(tert-butyl)triethylenetetramine, N,N'-bis-(methylisoamyl)ethylenediamine, N,N'-bis-(benzyl)ethylenediamine, N,N'-bis-(2-ethylhexyl)ethylenediamine, N,N'-bis-(4-methylbenzyl)ethylenediamine, N,N'-bis-(isopropyl)ethylenediamine, N,N'-bis-(3-methylbenzyl)ethylenediamine. The cross-linkers can be used alone or as mixtures of cross-linkers. Additional cross-linkers are known in the art, such as taught in patent publication US20080090922, incorporated herein by reference.

In another aspect the invention comprises a microcapsule wherein the shell comprises a reaction product of an isocyanate; and a multifunctional amine (meth)acrylate.

Useful benefit agent core materials include perfume raw materials, such as alcohols, ketones, aldehydes, esters, ethers, nitriles, alkenes, fragrances, fragrance solubilizers, essential oils, phase change materials, lubricants, colorants, cooling agents, preservatives, antimicrobial or antifungal actives, herbicides, antiviral actives, antiseptic actives, antioxidants, biological actives, deodorants, emollients, humectants, exfoliants, ultraviolet absorbing agents, self-healing compositions, corrosion inhibitors, sunscreens, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof. Phase change materials useful as core materials can include, by way of illustration and not limitation, paraffinic hydrocarbons having 13 to 28 carbon atoms, various hydrocarbons such n-octacosane, n-heptacosane, n-hexacosane, n-pentacosane, n-tetracosane, n-tricosane, n-docosane, n-heneicosane, n-eicosane, n-nonadecane, octadecane, n-heptadecane, n-hexadecane, n-pentadecane, n-tetradecane, n-tridecane. Phase materials can alternatively, optionally in addition include crystalline materials such as 2,2-dimethyl-1,3-propanediol, 2-hydroxymethyl-2-methyl-1, 3-propanediol, acids of straight or branched chain hydrocarbons such as eicosanoic acid and esters such as methyl palmitate, fatty alcohols and mixtures thereof.

The cross-linking functional monomer can be selected from tertiary-butylaminoethyl methacrylate, tertiary-butylaminopropyl methacrylate, n-butylaminoethyl methacrylate, diethylaminoethyl methacrylate, dimethylaminoethyl methacrylate, diisopropyaminoethyl methacrylate, dibutylaminoethyl methacrylate, dipropylaminoethyl methacrylate, tertiary pentylaminoethyl methacrylate, tertiary hexylaminoethyl methacrylate, tertiary-butylaminopropyl methacrylate, diethylaminopropyl methacrylate, and dimethylaminopropyl methacrylate.

Multifunctional acrylate or methacrylate monomers or oligomers can include mono-; di-; tri-; tetra-penta-; hexa-; hepta-; or octa-functional acrylate esters, methacrylate esters and multi-functional polyurethane acrylate esters and epoxy acrylates. Monomers shall be understood as including oligomers thereof. Optionally, an inhibitor such as hydroquinone can be added to the monomer and initiator blend in the capsules to prevent premature polymerization.

Useful in the invention are di- and poly-functional (meth)acrylate esters, difunctional (meth)acrylate esters, polyfunctional (meth)acrylate esters, difunctional urethane acrylate esters, polyfunctional urethane acrylate esters and polyfunctional and difunctional epoxy acrylate monomers and oligomers used alone or in combination as blends. In alternate embodiments, optionally, the di- and polyfunctional acrylates, methacrylates, urethane acrylates, and epoxy amine acrylates are further blended with monofunctional acrylates, methacrylates, urethane acrylates and epoxy acrylates.

Suitable isocyanates for use in the present invention can be selected from monomers and oligomers and blends, and can be $C_2$-$C_{24}$ linear, branched, cyclic, aromatic, or blends thereof.

Isocyanates suitable for use include but are not limited to di-isocyanates such as isophorone diisocyanate, also known as 3,3,5-trimethyl-5-isocyanato-methyl-cyclohexyl isocyanate or IPDI; hydrogenated materials such as cyclohexylene diisocyanate, 4,4'-methylenedicyclohexyl diisocyanate, 4,4'-methylene diphenyl diisocyanate ("MDI"), 2,2'-methylene diphenyl diisocyanate, 2,4'-methylene diphenyl diisocyanate (MDI), aralkyl diisocyanates such as tetramethylxylyl diisocyanates, polymethylene isocyanates such as 1,4-tetramethylene diisocyanate, 1,5-pentamethylene diisocyanate, 1,6-hexamethylene diisocyanate (HMDI), 1,7-heptamethylene diisocyanate, 2,2,4- and 2,4,4-trimethylhexamethylene diisocyanate, 1,10-decamethylene diisocyanate and 2-methyl-1,5-pentamethylene diisocyanate; and mixtures thereof.

Isocyanates can include aromatic isocyanates not limited to phenylene diisocyanate, toluene diisocyanate, xylene diisocyanate, 1,5-naphthalene diisocyanate, chlorophenylene 2,4-diisocyanate, bitoluene diisocyanate, dianisidine diisocyanate, tolidine diisocyanate, alkylated benzene diisocyanates, methylene-interrupted aromatic diisocyanates such as methylenediphenyl diisocyanate, 4,4'-isomer (MDI) including alkylated analogs such as 3,3'-dimethyl-4,4'-diphenylmethane diisocyanate, polymeric methylenediphenyl diisocyanate and mixtures thereof.

The invention is equally applicable to similar polyurethane compositions and processes. A microcapsule can be formed comprising an oil soluble or dispersible benefit agent core material. The microcapsule shell surrounding the oil core with benefit agent material is then a polyurethane formed from a first component of an isocyanate and a second component of a polyol. The polyol in this combination is a cross-linking functional monomer having cross-linking functional groups such as —OH, such as the reaction product of a hydroxyl(meth)acrylate and a multifunctional (meth)acrylate, together with a charge functional monomer such as a carboxy(meth)acrylate or quarternary ammonium acrylate. The carboxy(meth)acrylate and/or quarternary ammonium acrylate provide charged domains or charged pendant groups to the resultant polyurethane block copolymer helping drive the polymer to the interphase resulting in microcapsule shell formation surrounding the benefit agent dissolved or dispersed in droplets of the oil phase.

The invention makes possible tailored surface charge by chemical attachment through the charged domains or charged pendant groups of the resulting polymer.

The surface charge can improve the deposition of the microcapsules on substrates such as textiles, skin, hair, fibers, or other surfaces.

Surface charge can also be advantageously employed to improve adhesion of microcapsules on surfaces such as foam or bedding material.

Surface charge can also be advantageously adapted to create agglomerates to facilitate ease of filtration where a high solids, cake, or dry powder of microcapsules is desirable.

If desired the microcapsules can be separated from the aqueous medium. The slurry can either be used as is, used as a dewatered cake, or used in dry powder form depending on the application.

The polyol can be a hydroxyl(meth)acrylate selected from hydroxyalkyl(meth)acrylates such as hydroxyethyl(meth)acrylate or hydroxypropyl(meth)acrylate. The alkyl group can be any of $C_1$-$C_8$ carbons. The hydroxyl(meth)acrylate can also be hydroxy-substituted (meth)acrylates, such as alkylene glycol(meth)acrylate, and hydroxyl-substituted di- and tri-acrylates such as glycerol 1,3-diglycerate diacrylate.

The acrylate initiators are energy activated meaning generating free radicals when subjected to heat or other energy input such as actinic radiation or ion beam. Preferred initiators include peroxy initiators, azo initiators, peroxides, and compounds such as 2,2'-azobismethylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis (isobutylnitrile), 2,2'-azobis(2,4-dimethylpentanenitrile), 2,2'-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1'-azobis(cyanocyclohexane), benzoyl peroxide, decanoyl peroxide; lauroyl peroxide; benzoyl peroxide, di(n-propyl) peroxydicarbonate, di(sec-butyl) peroxydicarbonate, di(2-ethylhexyl) peroxydicarbonate, 1,1-dimethyl-3-hydroxybutyl peroxyneodecanoate, .alpha.-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy) hexane, t-amyl peroxy-2-ethylhexanoate, t-butyl peroxy-2-ethylhexanoate, t-butyl peroxyacetate, di-t-amyl peroxyacetate, t-butyl peroxide, di-t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like. Blends of initiators can also be employed. Initiators are available commercially, such as Vazo initiators, which typically indicate a decomposition temperature for the initiator. Preferably the initiator is selected to have a decomposition point of about 50° C. or higher. Usefully multiple initiators are employed, either as a blend in the oil phase, or in either of the oil or water phases. Preferably initiators are selected to stagger the decomposition temperatures at the various steps, pre-polymerization, wall formation and hardening or polymerizing of the capsule wall material. For example, a first initiator in the oil phase can decompose at 55° C., to promote prepolymer formation, a second can decompose at 60° C. to aid forming the wall material. Optionally a third initiator can decompose at 65° C. to facilitate polymerization of the capsule wall material. The total amount of initiator can be typically as low as 0.1 weight percent or as high as 10 weight percent.

The terms dispersed phase or oil phase are used interchangeably for purposes hereof and can be selected from hydrocarbons, more particularly hydrocarbon solvents and the solvents can include by way of illustration and not limitation, ethyldiphenylmethane, butyl biphenyl ethane, benzylxylene, alkyl biphenyls such as propylbiphenyl and butylbiphenyl, dialkyl phthalates e.g. dibutyl phthalate, dioctylphthalate, dinonyl phthalate and ditridecylphthalate; 2,2,4-trimethyl-1,3-pentanediol diisobutyrate, alkyl benzenes such as dodecyl benzene; but also carboxylates, ethers, or ketones such as diaryl ethers, di(aralkyl)ethers and aryl aralkyl ethers, ethers such as diphenyl ether, dibenzyl ether and phenyl benzyl ether, liquid higher alkyl ketones (having at least 9 carbon atoms), alkyl or aralky benzoates, e.g., benzyl benzoate, alkylated naphthalenes such as dipropylnaphthalene, partially hydrogenated terphenyls; high-boiling straight or branched chain hydrocarbons, arenes and alkaryl hydrocarbons such as toluene, vegetable oils such as canola oil, soybean oil, coin oil, sunflower oil, or cottonseed oil, methyl esters of fatty acids derived from transesterification of canola oil, soybean oil, cottonseed oil, corn oil, sunflower oil, pine oil, lemon oil, olive oil, or methyl ester of oleic acid, vegetable oils, esters of vegetable oils, e.g. soybean methyl ester, straight chain saturated paraffinic aliphatic hydrocarbons of from 10 to 13 carbons; $C_8$-$C_{42}$ esters, ethyl hexanoate, methyl heptanoate, butyl butyrate, methyl benzoate, methyl such as nonoate, methyl decanoate, methyl dodecanoate, methyl octanoate, methyl laurate, methyl myristate, methyl palmitate, methyl stearate, ethyl heptanoate, ethyl octanoate, ethyl nonoate, ethyl decanoate, ethyl dodecanoate, ethyl laurate, ethyl myristate, ethyl palmitate, ethyl stearate, isopropyl myristate, isopropyl palmitate, ethylhexyl palmitate, isoamyl laurate, butyl laurate, octyl octanoate, decyl decanoate, butyl stearate, lauryl laurate, stearyl palmitate, stearyl stearate, stearyl behenate, and behenyl behenate. Mixtures of the above can also be employed. Common diluents such as straight chain hydrocarbons can also be blended with the solvents, or blend of solvents. The solvent is selected on the basis of hydrophobicity and ability to disperse or solvate the isocyanate.

The process of the invention provides a robust benefit agent delivery particle. The benefit agent delivery particle is a microcapsule of shell surrounding a core material. The process of forming the microcapsule comprises forming divided water phases, preferably involving providing a first composition of water phase 1, a water phase 2 and a water phase 3. Water phase 1 comprises water and an initiator. Water phase 2 comprises water, a water-soluble or dispersible amine(meth)acrylate and a multifunctional (meth)acrylate. Water phase 3 comprises water and carboxy-substituted alkyl (meth)acrylate, and optionally a base. In one embodiment, in a first step, the combined (meth)acrylate) monomers are pre-reacted to form a multifunctional amine(meth) acrylate pre-polymer.

An emulsion is formed by emulsifying under high shear agitation a second composition into the first composition;

the second composition comprising an oil phase comprising an isocyanate and a benefit agent core material.

The emulsion is heated in one or more steps to form a wall material comprising the reaction product of the isocyanate and multifunctional amine(meth)acrylate, the wall surrounding the benefit agent core material.

In the process and composition of the invention, charge can be tailored to a high zeta potential at pH of 7, to a zeta potential in the range of from +70 to −70, and advantageously in many applications a range of from +40 to −65 is useful. Preferred is a zeta potential of greater than +70, or greater than +40, or greater than −70, or even greater than −40. Useful is a zeta potential of from +70 to +20, or from −20 to −70; or even a zeta potential of from +70 to +40, or from −40 to −70; or even from +70 to +50, or even from −50 to −70. "Greater than" or "higher than" in this context means a higher charge value, whether positive of negative. A more positive (greater positive value) or more negative charge value (greater negative value) is preferred.

Optionally, deposition aids can be included to increase deposition or adhesion of the microcapsules to various surfaces such as various substrates including but not limited to paper, fabric skin, hair, towels, or other surfaces. Deposition aids can include poly (acrylamide-co-diallyldimethylammonium chloride, poly (diallyldimethylammonium chloride, polyethylenimine, cationic polyamine, poly [(3-methyl-1-vinylimidazolium chloride)-co-(1-vinylpyrrolidone)], copolymer of acrylic acid and diallyldimethylammonium chloride, cationic guar, guar gum, an organopolysiloxane such as described in US Publication 20150030557, incorporated herein by reference. In a further embodiment, the above-described microcapsules can comprise a deposition aid, and in a further aspect the deposition aid coats the outer surface of the shell of the microcapsule.

In a further aspect the deposition aid can comprise a material selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In a yet further aspect, the deposition aid comprises a material selected from the group consisting of poly(meth)acrylates, poly(ethylene-maleic anhydride), polyamine, polyvinylpyrrolidone, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polysiloxane, poly(propylene maleic anhydride), maleic anhydride derivatives, co-polymers of maleic anhydride derivatives, polyvinyl alcohol, carboxymethyl cellulose, carboxymethyl hydroxyethyl cellulose, hydroxyethyl cellulose, polyvinyl methyl ether/maleic anhydride, polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof.

In the following examples, the abbreviations correspond to the following materials:

TABLE 1

| | Company/City | |
|---|---|---|
| V50 | Wako Specialty Chemicals, Richmond, VA | 2,2'-azobis (2-methylpropionamidine) dihydrochloride |
| SR415 | Sartomer Company, Exton, PA | Ethoxylated trimethylolpropane triacrylate |
| CD9055 | Sartomer Company, Exton, PA | Carboxylic acid monofunctional acrylate monomer |
| SR344 | Sartomer Company, Exton, PA | Polyethylene glycol diacrylate |
| SR603 | Sartomer Company, Exton, PA | Polyethylene glycol dimethacrylate |
| DETA | Dow Chemical Company, Midland, MI | Diethylene triamine |
| TBAEMA | Sigma Aldirch, St. Louis, MO | 2-(tert-butylamino) ethyl methacrylate |
| HEMA | | hydroxyethylmethacrylate |
| TMACEMA | | 2-(methacryloxyethyl)trimethyl ammonium chloride |

Example 1

Polymer Preparation Process: For water phase 1, 0.5 grams water-soluble initiator (V50) is added to 200 g water in the jacketed steel reactor at 40° C. with mixing at 1000 rpm and a nitrogen blanket at 100 cc/min. The solution is heated from 40° C. to 75° C. in 45 minutes, held at 75° C. for 45 minutes and cooled to 60° C. in 75 minutes. A 150 g water phase 2, which includes 2.5 g of at least one multifunctional water dispersible acrylic monomer (SR415), and 10 grams of at least one water-soluble acrylic monomer with cross-linking functional groups (i.e. TBAEMA) is added, and the mixing is increased to 1500 rpm. The combined water phases are mixed for 60 minutes at 60° C. and then 150 g water phase 3, which includes 12.5 grams of at least one water-soluble acrylic monomer with a surface charge functional group (CD9055), is added and the combined solutions held at 60° C. for another 30 minutes. The solution is then heated to 75° C. in 30 minutes, heated from 75° C. to 95° C. in 7 hours, and held at temperature for 6 hours to form the finished polymer.

Example 1A

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for 240 minutes, and is heated to 85° C. in 60 minutes, and is held at 85° C. for 240 minutes. After the heating cycle, the temperature is set to return to room temperature.

Example 1B

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for an additional 20 minutes and 1.8 g of additional cross-linker (DETA) is added. The batch is then held at 60° C. for another 120 minutes, is heated to 85° C. in 60 minutes, and held at 85° C. for 240 minutes. After the heating cycle is complete the temperature is set to return to room temperature.

Example 1C

The batch is made using a Caframo BDC6015 mixer, Finemech KGW-2205 tempering beaker (reactor) and a Cole Parmer re-circulating, heating water bath. For the internal phase, 75 g oil is placed in a beaker and mixed with 25 g of Desmodur W (H12MDI) using a stir plate until homogenous. The water phase preparation is begun in the reactor by adding 18.11 g of acrylate anionic polymer (preparation described above) and 7.75 g Evonik OX50 hydrophilic silica to 284.14 g water, mixing for 15 minutes with the re-circulating water bath set to 35° C. After the water phase has mixed, the internal phase is added over 1 minute to the reactor and the speed of the Caframo is set to 3000 rpm to start milling. At the end of one hour of milling, the mixer is turned off and the mill blade is replaced with a z-bar. The speed is then set to 350 rpm and the batch is heated to 92° C. and held there for 12 hours, after which the temperature is set to return to room temperature.

Example 1D

For this lab batch process, the batch is made using a Caframo BDC6015 mixer, Finemech KGW-2205 tempering beaker (reactor) and a Cole Parmer re-circulating, heating water bath. For the internal phase, 240 g oil is placed in a beaker and mixed with 3.0 g of Desmodur N3300A and 7.0 g of Desmodur N3400 using a stir plate until homogenous. The water phase preparation is begun in the reactor by adding 33.1 g of acrylate anionic polymer (preparation described above) to 179.0 g water, mixing for 15 minutes with the re-circulating water bath set to 35° C. After the water phase has mixed, the Caframo mixer is increased to 2000 rpm and the internal phase is added over 2 minutes to the reactor. When all of the internal phase has been added, the speed of the Caframo is set to 3000 rpm to start milling. At the end of milling, the mixer is turned off and the mill blade is replaced with a z-bar. The speed is then set to 500 rpm and the re-circulating water bath is set to 40° C. for two hours. Then the water bath temperature is increased to 60° C. and held for 3 hours, after which the temperature is set to return to room temperature.

The final encapsulation of all samples could contain a polyacrylate/polyurea dual component wall system with a surface charge functional group. The capsule is anionic and exhibits low leakage.

Example 2

Polymer Preparation Process: For water phase 1, 0.825 grams water-soluble initiator (V50) is added to 200 g water in the jacketed steel reactor at 40° C. with mixing at 1000 rpm and a nitrogen blanket at 100 cc/min. The solution is heated from 40° C. to 75° C. in 45 minutes, held at 75° C. for 45 minutes and cooled to 60° C. in 75 minutes. A 150 g water phase 2, which includes 2.5 g of at least one multifunctional water dispersible acrylic monomer (SR415), and 10 grams of at least one water-soluble acrylic monomer with cross-linking functional groups (i.e. hydroxyethylmethacrylate (HEMA)) is added, and mixing is increased to 1500 rpm. The combined water phases are mixed for 60 minutes at 60° C. and then 150 g water phase 3, which includes 15 grams of at least one water-soluble acrylic monomer with a surface charge functional group (CD9055), is added and the combined solutions held at 60° C. for another 30 minutes. The solution is then heated to 75° C. in 30 minutes, heated from 75° C. to 95° C. in 7 hours, and is held at 95° C. for 6 hours to form the finished polymer.

Example 2A

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, held at 60° C. for 240 minutes, heated to 85° C. in 60 minutes, and held at 85° C. for 240 minutes. After the heating cycle is completed, the temperature is set to return to room temperature.

Example 2B

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm, the batch is heated to 60° C. in 120 minutes, held at 60° C. for 120 minutes, and 1.8 g of additional cross-linker (DETA) is added. Batch heating is continued at 60° C. for 120 minutes, the batch is heated to 85° C. in 60 minutes, and held at 85° C. for 240 minutes. After the heating cycle is completed the temperature is set to return to room temperature.

The microcapsules contain a polyacrylate/polyurea/polyurethane tri-component wall with a surface charge functional group. The microcapsule is anionic and exhibits low leakage

Example 3

Polymer Preparation Process: For water phase 1, 0.5 grams water-soluble initiator (V50) is added to 200 g water in the jacketed steel reactor at 40° C. with mixing at 1000 rpm and a nitrogen blanket at 100 cc/min. The solution is heated from 40° C. to 75° C. in 45 minutes, held at 75° C. for 45 minutes and cooled to 60° C. in 75 minutes. A 150 g water phase 2, which includes 5 g of at least one multifunctional water dispersible acrylic monomer (SR415) and 5.5 grams of at least one water-soluble acrylic monomer with cross-linking functional groups (i.e. TBAEMA) is added, and mixing is increased to 1500 rpm. The combined water phases are mixed for 60 minutes at 60° C. and then 150 g water phase 3, which includes 12.5 grams of at least one water-soluble acrylic monomer with a surface charged functional group (i.e. 2-(methacryloyloxy) ethyl]trimethylammonium chloride), is added and the combined solutions held at 60° C. for another 30 minutes. The solution is then heated to 75° C. in 30 minutes, heated from 75° C. to 95° C. in 7 hours, and held at 95° C. for 6 hours to form the finished polymer.

Example 3A

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate cationic polymer (preparation described above) to 144 g water, mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for 240 minutes, is heated to 85° C. in 60 minutes, and is held at 85° C. for 240 minutes. After the heating cycle is completed the temperature is set to return to room temperature.

Example 3B

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and Mondur MR (MDI) using a stir plate until homogenous. The water phase preparation is begun in the reactor by adding 6 g of acrylate cationic polymer (preparation described above) to 144 g water and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for 120 minutes, and 1.8 g of additional cross-linker (DETA) is added. Batch heating is continued at 60° C. for 120 minutes, and the batch is heated to 85° C. in 60 minutes, and held at 85° C. for 240 minutes. After the heating cycle is completed the temperature is set to return to room temperature.

The microcapsules contain a polyacrylate/polyurea dual component wall system with a surface charged functional group. The capsule is cationic and exhibits low leakage.

Example 4

Polymer Preparation Process: For water phase 1, 0.5 grams water-soluble initiator (V50) is added to 200 g water in the jacketed steel reactor at 40° C. with mixing at 1000 rpm and a nitrogen blanket at 100 cc/min. The solution is heated from 40° C. to 75° C. in 45 minutes, held at 75° C. for 45 minutes and cooled to 60° C. in 75 minutes. A 150 g water phase 2, which includes 2.5 g of at least one multifunctional water dispersible acrylic monomer (SR415), and 10 grams of at least one water-soluble acrylic monomer with cross-linking functional groups (i.e. TBAEMA) is added, and the mixing is increased to 1500 rpm. The combined water phases are mixed for 60 minutes at 60° C. and then 150 g water phase 3, which includes 12.5 grams of at least one water-soluble acrylic monomer with a surface charge functional group (2-sulfoethyl methacrylate) with pH adjusting to 6.0, is added and the combined solutions held at 60° C. for another 30 minutes. The solution is then heated to 75° C. in 30 minutes, heated from 75° C. to 95° C. in 7 hours, and held at temperature for 6 hours to form the finished polymer.

Example 4

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for 240 minutes, and is heated to 85° C. in 60 minutes, and is held at 85° C. for 240 minutes. After the heating cycle, the temperature is set to return to room temperature.

The final encapsulation of all samples could contain a polyacrylate/polyurea dual component wall system with a surface charge functional group. The microcapsule is pH-independent anionic and exhibits low leakage.

Example 5

Polymer Preparation Process: For water phase 1, 0.5 grams water-soluble initiator (V50) is added to 200 g water in the jacketed steel reactor at 40° C. with mixing at 1000 rpm and a nitrogen blanket at 100 cc/min. The solution is heated from 40° C. to 75° C. in 45 minutes, held at 75° C. for 45 minutes and cooled to 60° C. in 75 minutes. A 150 g water phase 2, which includes 2.5 g of at least one multi-functional water dispersible acrylic monomer (Ethoxylated trimethylolpropane triacrylate, such as SR9035 or SR502), and 10 grams of at least one water-soluble acrylic monomer with cross-linking functional groups (i.e. TBAEMA) is added, and the mixing is increased to 1500 rpm. The combined water phases are mixed for 60 minutes at 60° C. and then 150 g water phase 3, which includes 12.5 grams of at least one water-soluble acrylic monomer with a surface charge functional group (CD9055), is added and the combined solutions held at 60° C. for another 30 minutes. The solution is then heated to 75° C. in 30 minutes, heated from 75° C. to 95° C. in 7 hours, and held at temperature for 6 hours to form the finished polymer.

Example 5A

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for 240 minutes, and is heated to 85° C. in 60 minutes, and is held at 85° C. for 240 minutes. After the heating cycle, the temperature is set to return to room temperature.

Example 5B

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for an additional 20 minutes and 1.8 g of additional cross-linker (DETA) is added. The batch is then held at 60° C. for another 120 minutes, is heated to 85° C. in 60 minutes, and held at 85° C. for 240 minutes. After the heating cycle is complete the temperature is set to return to room temperature.

The final encapsulation of all samples could contain a polyacrylate/polyurea dual component wall system with a surface charge functional group. The microcapsule is anionic and exhibits low leakage.

Example 6

Polymer Preparation Process: For water phase 1, 0.5 grams water-soluble initiator (V50) is added to 200 g water in the jacketed steel reactor at 40° C. with mixing at 1000 rpm and a nitrogen blanket at 100 cc/min. The solution is heated from 40° C. to 75° C. in 45 minutes, held at 75° C. for 45 minutes and cooled to 60° C. in 75 minutes. A 150 g water phase 2, which includes 2.5 g of at least one multi-functional water dispersible acrylic monomer (polyethylene glycol diacrylate, such as SR344 or SR601), and 10 grams of at least one water-soluble acrylic monomer with cross-linking functional groups (i.e. TBAEMA) is added, and the mixing is increased to 1500 rpm. The combined water phases are mixed for 60 minutes at 60° C. and then 150 g water phase 3, which includes 12.5 grams of at least one water-soluble acrylic monomer with a surface charge functional group (CD9055), is added and the combined solutions held at 60° C. for another 30 minutes. The solution is then heated to 75° C. in 30 minutes, heated from 75° C. to 95° C. in 7 hours, and held at temperature for 6 hours to form the finished polymer.

Example 6A

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for 240 minutes, and is heated to 85° C. in 60 minutes, and is held at 85° C. for 240 minutes. After the heating cycle, the temperature is set to return to room temperature.

Example 6B

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for an additional 20 minutes and 1.8 g of additional cross-linker (DETA) is added. The batch is then held at 60° C. for another 120 minutes, is heated to 85° C. in 60 minutes, and held at 85° C. for 240 minutes. After the heating cycle is complete the temperature is set to return to room temperature.

The final encapsulation of all samples could contain a polyacrylate/polyurea dual component wall system with a surface charge functional group. The microcapsule is pH-independent anionic and exhibits low leakage.

Example 7

Polymer Preparation Process: For water phase 1, 0.5 grams water-soluble initiator (V50) is added to 200 g water in the jacketed steel reactor at 40° C. with mixing at 1000 rpm and a nitrogen blanket at 100 cc/min. The solution is heated from 40° C. to 75° C. in 45 minutes, held at 75° C. for 45 minutes and cooled to 60° C. in 75 minutes. A 150 g water phase 2, which includes 2.5 g of at least one multi-functional water dispersible acrylic monomer (polyethylene glycol dimethacrylate such as SR603), and 10 grams of at least one water-soluble acrylic monomer with cross-linking functional groups (i.e. TBAEMA) is added, and the mixing is increased to 1500 rpm. The combined water phases are mixed for 60 minutes at 60° C. and then 150 g water phase 3, which includes 12.5 grams of at least one water-soluble acrylic monomer with a surface charge functional group (CD9055), is added and the combined solutions held at 60° C. for another 30 minutes. The solution is then heated to 75° C. in 30 minutes, heated from 75° C. to 95° C. in 7 hours, and held at temperature for 6 hours to form the finished polymer.

Example 7A

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for 240 minutes, and is heated to 85° C. in 60 minutes, and is held at 85° C. for 240 minutes. After the heating cycle, the temperature is set to return to room temperature.

Example 7B

The batch is made using a Caframo BDC6015 mixer, Finemech KGW-2205 tempering beaker (reactor) and a Cole Parmer re-circulating, heating water bath. For the internal phase, 90 g oil phase is placed in a beaker and mixed with 7.78 g Desmodur I (IPDI) and 3.35 g Mondur MR (MDI) using a stir plate until homogenous. The water phase preparation is begun in the reactor by adding 6 g of acrylate anionic polymer (preparation described above) to 144 g water, and mixing for 30 minutes with the re-circulating water bath set to 7° C. After the water phase is mixed, the internal phase is added over 1 minute to the reactor and the speed of the Caframo is set to 2500 rpm to start milling to form a stable emulsion at target size (i.e. 10 um). At the end of milling, the mixer is turned off and the mill blade is replaced with a z-bar. The mixing speed is then set to 200 rpm and the batch is heated to 60° C. in 120 minutes, is held at 60° C. for an additional 20 minutes and 1.8 g of additional cross-linker (DETA) is added. The batch is then held at 60° C. for another 120 minutes, is heated to 85° C. in 60 minutes, and held at 85° C. for 240 minutes. After the heating cycle is complete the temperature is set to return to room temperature.

The final encapsulation of all samples could contain a polyacrylate/polyurea dual component wall system with a surface charge functional group. The microcapsule is pH-independent anionic and exhibits low leakage.

Example 8: Characterization of the Properties of Microcapsules

Characterization of free oil in microcapsule suspension: 1 g of the microcapsule suspension (40% solid) was mixed with 10 ml of Hexanes/DBP solution by using the automated volume dispenser to leach the free oil from microcapsule suspension, and then sited on the counter for 30 minutes. 1 ml of top, clear Hexanes/DBP layer was carefully pipetted, and measured by Agilent 6890N Gas chromatography (GC) to determine the free oil in suspension. The free oil results are shown in Table 1 below:

TABLE 1

| | Sample | | | | | | |
|---|---|---|---|---|---|---|---|
| | 1A | 1B | 1C | 2A | 2B | 3A | 3B |
| Free Oil (%) | 0.07 | 0.03 | 0.06 | 0.11 | 0.02 | 0.07 | 0.03 |

The low free oil of all the tested samples indicates a successful microencapsulation process which can encapsulate core materials highly efficiency with extremely low leakage.

Characterization of leakage of core of microcapsule in Hexane: microcapsule suspension (including 1.5 g core material) was mixed with 47 ml of de-ionized water in a 150 ml jar to form homogenous suspension. 50 mL of Hexane w/DBP was gently add to the jar and cap tightly. At t=24, 1 week, 2 weeks and 4 weeks, the upper hexane layer was carefully pipetted, and the extraction was measured by Agilent 6890N Gas chromatography (GC) to determine leakage of the microcapsule suspension in different time point. The leakage results are shown in FIG. 1. The long-term leakage (up to 4 weeks) in hexane results exhibit these microcapsules can be very stable in organic solvent, especially these samples with additional crosslinker (DETA). The results indicate the multi component wall systems are highly resistant to organic solvent system.

Characterization of surface charge of microcapsule samples: 10 g of microcapsule aqueous suspension (4% solid) was added in well-cleaned sample cup, and the pH was adjusted to 10 by 0.1N NaOH. The pH of aqueous suspension was slowly adjusted from 10 to 3 by using 0.1N HCl with 10 ul/min, and the surface charge of microcapsule samples was measured by Microtrac Stabino Particle Charge Titration Analyzer, and shown in FIGS. 2, 3, 4, and 5. The test results exhibit that the microcapsules samples can have permanent charge on their surface area, and more important, the surface charge can be tailored by using different acrylic monomer with charge functional group. The sample 1 and 2 has pH-dependent anionic surface charge due to the carboxyl group from CD9055, and the sample 4 has pH-independent anionic surface charge due to the sulfate group from 2-sulfoethyl methacrylate, while the cationic surface charge of sample 3 comes from the trimethylammonium group from 2-(methacryloyloxy)ethyl] trimethylammonium chloride.

All documents cited in the specification herein are, in relevant part, incorporated herein by reference for all jurisdictions in which such incorporation is permitted. The citation of any publication is for its disclosure prior to the filing date and should not be construed as an admission that such publication is prior art or that the present invention is not entitled to antedate such publication by virtue of prior invention. To the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. No unclaimed language should be deemed to limit the invention in scope. Any statements or suggestions herein that certain features constitute a component of the claimed invention are not intended to be limiting unless reflected in the appended claims.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive variations and charges can be made by those skilled in the art without departing from the spirit and scope of the invention.

What we claim is:

1. A microcapsule having a shell containing surface charge functional groups, the microcapsule made by a process comprising:
    dispersing in one or more water phases an initiator, a cross-linking functional monomer having one or more —OH, —NH$_2$, or —NH groups, and a charge functional monomer having one or more anionic or cationic groups which are selected from carboxy, sulfonic acid, quaternary ammonium groups, or other charged groups;
    prereacting the monomers in the one or more water phases and combining with a water dispersible multifunctional (meth)acrylate monomer;
    further prereacting the combined monomers; forming an emulsion by emulsifying into the water phase or phases, using high shear agitation, an oil phase comprising an isocyanate and a benefit agent core material;
    optionally adding in addition, an amine cross-linker;
    further reacting the combined emulsion of prereacted monomers, water dispersible multifunctional (meth) acrylate monomer, and emulsified oil phase by heating for a time and temperature, or actinic irradiation for a time, sufficient to form a microcapsule shell having a surface charge, said microcapsule shell surrounding the benefit agent core material.

2. The microcapsule according to claim 1 wherein the cross-linking functional monomer is an amine.

3. The microcapsule according to claim 2 wherein the amine is an alkylaminoalkyl(meth)acrylate.

4. The microcapsule according to claim 1 wherein the cross-linking functional monomer is hydroxyl functional.

5. The microcapsule according to claim 4 wherein the cross-linking functional monomer is a hydroxyl(meth)acrylate.

6. A microcapsule having a shell with surface charge functional groups, the microcapsule comprising an oil soluble or dispersible benefit agent core material and a shell surrounding the benefit agent core material, the shell comprising a polyurea formed from a first component of an isocyanate and a second component of an amine, the amine comprising the reaction product of an alkylaminoalkyl (meth)acrylate and a multifunctional (meth)acrylate, together with a carboxyalkyl(meth)acrylate or quarternary ammonium acrylate.

7. The microcapsule according to claim 6 wherein the amine is tertiary-butylaminoethylmethacrylate.

8. A microcapsule according to claim 6 wherein the shell comprises a reaction product of an isocyanate; and a multifunctional amine (meth)acrylate.

9. The microcapsule according to claim 6 wherein the isocyanate is selected from isophorone diisocyanate, 4,4'-methylene diphenyl diisocyanate, 2,2'-methylene diphenyl diisocyanate, and 2,4'-methylene diphenyl diisocyanate.

10. The microcapsule according to claim 6 wherein the alkylaminoalkyl (meth)acrylate is selected wherein each alkyl moiety is independently from $C_1$ to $C_8$.

11. The microcapsule according to claim 6 wherein the alkylamino (meth)acrylate is selected from tertiary-butylaminoethyl methacrylate, tertiary-butylaminopropyl methacrylate, n-butylaminoethyl methacrylate, diethylaminoethyl methacrylate, dimethylaminoethyl methacrylate, diisopropyaminoethyl methacrylate, dibutylaminoethyl methacrylate, dipropylaminoethyl methacrylate, tertiary pentylaminoethyl methacrylate, tertiary hexylaminoethyl methacrylate, tertiary-butylaminopropyl methacrylate, diethylaminopropyl methacrylate, and dimethylaminopropyl methacrylate.

12. The microcapsule according to claim 6 wherein the microcapsule has a zeta potential, measured at a pH of 7, of from +70 to −70.

13. The microcapsule according to claim 6 wherein the benefit agent core material is selected from one or more of a fragrance, perfume, phase change material, biological active, antimicrobial, self-healing composition, lubricant or cooling agent.

14. A microcapsule having a shell with surface charge functional groups, the microcapsule comprising an oil soluble or dispersible benefit agent core material and a shell surrounding the benefit agent core material, the shell comprising a reaction product of an isocyanate; and a multifunctional amine (meth) acrylate, together with a carboxyalkyl (meth)acrylate, wherein the multifunctional amine(meth) acrylate is selected to be polar.

15. A microcapsule having a shell with surface charge functional groups, the microcapsule comprising an oil soluble or dispersible benefit agent core material and a shell surrounding the benefit agent core material, the shell comprising a polyurethane formed from a first component of an isocyanate and a second component of a polyol, the polyol comprising the reaction product of a hydroxy(meth)acrylate and a multifunctional (meth)acrylate, together with a carboxyalkyl(meth)acrylate or quarternary ammonium acrylate.

16. The microcapsule according to claim 15 wherein the hydroxyl(meth)acrylate is hydroxyethyl(meth)acrylate.

17. A microcapsule according to claim 15 wherein the shell comprises a reaction product of an isocyanate; and a multifunctional hydroxy(meth)acrylate.

18. The microcapsule according to claim 15 wherein the isocyanate is selected from isophorone diisocyanate, 4,4'-methylene diphenyl diisocyanate, 2,2'-methylene diphenyl diisocyanate, and 2,4'-methylene diphenyl diisocyanate.

19. The microcapsule according to claim 15 wherein the hydroxy (meth)acrylate is a hydroxyl(meth)acrylate and the alkyl moiety of the hydroxyalkyl(meth)acrylate is selected from $C_1$ to $C_{24}$.

20. The microcapsule according to claim 15 wherein the hydroxy(meth)acrylate is selected from hydroxyalkyl(meth) acrylate, alkylene glycol(meth)acrylate, alkylene glycol (meth)acrylate and glycerol 1,3-diglycerate diacrylate.

21. The microcapsule according to claim 15 wherein the microcapsule has a zeta potential, measured at a pH of 7, of from +70 to −70.

22. The microcapsule according to claim 15 wherein the benefit agent core material is selected from one or more of a fragrance, perfume, phase change material, biological active, antimicrobial, self-healing composition, lubricant or cooling agent.

23. A microcapsule having a shell with surface charge functional groups, the microcapsule comprising an oil soluble or dispersible benefit agent core material and a shell surrounding the benefit agent core material, the shell comprising a reaction product of an isocyanate; and a multifunctional polyol (meth) acrylate, together with a carboxyalkyl (meth)acrylate, wherein the multifunctional polyol(meth) acrylate is selected to be polar.

24. A process of making a benefit agent delivery particle, said process comprising providing a first composition of water phase 1, water phase 2 and water phase 3:
water phase 1 comprising water and an initiator;
water phase 2 comprising water, a cross-linking functional monomer comprising a water-soluble or dispersible amine(meth)acrylate or hydroxy(meth)acrylate and a water-soluble or dispersible multifunctional (meth) acrylate;
water phase 3 comprising water, carboxyalkyl(meth)acrylate and a base, or quarternary ammonium alkyl acrylate;
combining water phase 1 and water phase 2;
pre-reacting the amine(meth)acrylate or hydroxyl(meth) acrylate and the multifunctional (meth)acrylate of the combined water phases to form a multifunctional amine (meth)acrylate or hydroxyl(meth)acrylate pre-polymer;
combining the pre-polymer with water phase 3;
further prereacting the combined pre-polymer;
forming an emulsion by emulsifying under high shear agitation a second composition into said first composition; the second composition comprising an oil phase comprising an isocyanate and a benefit agent core material;
optionally adding in addition, an amine cross-linker;
heating in one or more steps said emulsion to form a shell material comprising the reaction product of the isocyanate and the prepolymer, the shell material surrounding the benefit agent core material.

25. The process according to claim 24 wherein the microcapsule has a zeta potential, measured at a pH of 7, of from +70 to −70.

26. The process according to claim 24 wherein the amine (meth)acrylate is an alkylaminoalkyl (meth)acrylate and wherein each alkyl moiety independently is from $C_1$ to $C_8$.

27. A process of making a benefit agent delivery particle, said process comprising providing a first composition of water phase 1, water phase 2 and water phase 3:
water phase 1 comprising water and an initiator;
water phase 2 comprising water, a cross-linking functional monomer comprising a water-soluble or dispersible hydroxyl(meth)acrylate and a water-soluble or dispersible multifunctional (meth)acrylate;
water phase 3 comprising water, carboxyalkyl(meth)acrylate and a base, or quarternary ammonium alkyl acrylate;
combining water phase 1 and 2;
pre-reacting the amine(meth)acrylate or hydroxyl(meth) acrylate and the multifunctional (meth)acrylate of the combined water phases to form a hydroxy (meth) acrylate pre-polymer;
combining the pre-polymer with water phase 3;
further prereacting the combined pre-polymer;
forming an emulsion by emulsifying under high shear agitation a second composition into said first composition; the second composition comprising an oil phase comprising an isocyanate and a benefit agent core material;
optionally adding in addition, an amine cross-linker;
heating in one or more steps said emulsion to form a shell material comprising the reaction product of the isocyanate and the prepolymer, the shell material surrounding the benefit agent core material, the shell having surface charge functional groups.

28. The process according to claim 27 wherein the microcapsule has a zeta potential, measured at a pH of 7, of from +70 to −70.

29. The process according to claim 27 wherein the amine (meth)acrylate is an alkylaminoalkyl (meth)acrylate and wherein each alkyl moiety independently is from $C_1$ to $C_8$.

30. The process according to claim 27 wherein the hydroxy(meth)acrylate is selected from hydroxyalkyl(meth)acrylate, alkylene glycol(meth)acrylate, alkylene glycol (meth)acrylate and glycerol 1,3-diglycerate diacrylate.

31. The process according to claim 27 wherein the microcapsule has a zeta potential, measured at a pH of 7, of a higher positive value than +40 or greater negative value than −40.

* * * * *